US010111961B2

(12) United States Patent
Bouchemal

(10) Patent No.: US 10,111,961 B2
(45) Date of Patent: Oct. 30, 2018

(54) SELF-ASSOCIATING MICROPARTICLES AND NANOPARTICLES CONSISTING OF PROTEINS

(71) Applicants:CENTRE NATIONAL DE LA RECHERCHE SCIENTIFIQUE, Paris (FR); UNIVERSITE PARIS-SUD XI, Orsay (FR)

(72) Inventor: Kawthar Bouchemal, Palaiseau (FR)

(73) Assignees: CENTRE NATIONAL DE LA RECHERCHE SCIENTIFIQUE, Paris (FR); UNIVERSITE PARIS-SUD XI, Orsay (FR)

( * ) Notice: Subject to any disclaimer, the term of this patent is extended or adjusted under 35 U.S.C. 154(b) by 100 days.

(21) Appl. No.: 14/894,708

(22) PCT Filed: May 2, 2014

(86) PCT No.: PCT/FR2014/051052
§ 371 (c)(1),
(2) Date: Nov. 30, 2015

(87) PCT Pub. No.: WO2014/191645
PCT Pub. Date: Dec. 4, 2014

(65) Prior Publication Data
US 2016/0120991 A1 May 5, 2016

(30) Foreign Application Priority Data
May 31, 2013 (FR) ...................................... 13 55003

(51) Int. Cl.
| A61K 47/42 | (2017.01) |
| A61K 8/64 | (2006.01) |
| A61K 8/65 | (2006.01) |
| A61K 8/67 | (2006.01) |
| A61K 47/40 | (2006.01) |
| A61K 8/11 | (2006.01) |
| A61Q 19/02 | (2006.01) |
| A61Q 19/04 | (2006.01) |
| A61Q 19/06 | (2006.01) |
| A61Q 19/08 | (2006.01) |
| A61Q 19/10 | (2006.01) |
| C08B 37/16 | (2006.01) |
| A61K 47/48 | (2006.01) |
| C08H 1/00 | (2006.01) |
| A61Q 13/00 | (2006.01) |
| A61Q 15/00 | (2006.01) |
| A61Q 17/04 | (2006.01) |
| A61K 8/73 | (2006.01) |
| A61Q 19/00 | (2006.01) |
| A61K 38/16 | (2006.01) |
| A61K 38/39 | (2006.01) |
| A61K 9/50 | (2006.01) |

(52) U.S. Cl.
CPC ................ *A61K 47/42* (2013.01); *A61K 8/11* (2013.01); *A61K 8/64* (2013.01); *A61K 8/645* (2013.01); *A61K 8/65* (2013.01); *A61K 8/738* (2013.01); *A61K 9/5036* (2013.01); *A61K 9/5052* (2013.01); *A61K 9/5057* (2013.01); *A61K 38/168* (2013.01); *A61K 38/39* (2013.01); *A61K 47/40* (2013.01); *A61K 47/48969* (2013.01); *A61Q 13/00* (2013.01); *A61Q 15/00* (2013.01); *A61Q 17/04* (2013.01); *A61Q 19/00* (2013.01); *A61Q 19/008* (2013.01); *A61Q 19/02* (2013.01); *A61Q 19/04* (2013.01); *A61Q 19/06* (2013.01); *A61Q 19/08* (2013.01); *A61Q 19/10* (2013.01); *C08B 37/0015* (2013.01); *C08H 1/00* (2013.01); *A61K 2800/56* (2013.01)

(58) Field of Classification Search
None
See application file for complete search history.

(56) References Cited

U.S. PATENT DOCUMENTS

| 4,363,760 A | 12/1982 | Cioca |
| 4,659,740 A | 4/1987 | Usher |
| 4,670,419 A * | 6/1987 | Uda ...................... A61K 47/40 514/10.1 |
| 5,679,657 A | 10/1997 | Oka et al. |
| 7,893,040 B2 * | 2/2011 | Loftsson .............. A61K 9/0043 514/54 |

(Continued)

FOREIGN PATENT DOCUMENTS

| FR | 2 739 860 A1 | 4/1997 |
| JP | 2003 267817 A | 9/2003 |

(Continued)

OTHER PUBLICATIONS

Irie, T., et al., "Cyclodextrins in peptide and protein delivery", Adv. Drug Deliv. Rev., 1999, pp. 101-123.*

(Continued)

*Primary Examiner* — Michael G Hartley
*Assistant Examiner* — Lance W Rider
(74) *Attorney, Agent, or Firm* — Young & Thompson

(57) ABSTRACT

Microparticles and nanoparticles of hydrophobized proteins and an alpha-cyclodextrin, obtained by auto-association in an aqueous medium, the hydrophobized protein being obtained by grafting of alkyl chains coming from fatty acids, by an acylation reaction. These microparticles and nanoparticles constitute systems used for encapsulation of active substances of interest, in particular in the pharmaceutical field, and the vectorization thereof for therapeutic purposes.

7 Claims, 7 Drawing Sheets

(56) References Cited

U.S. PATENT DOCUMENTS

| | | | |
|---|---|---|---|
| 2002/0143171 | A1 | 10/2002 | Yui et al. |
| 2008/0220030 | A1 | 9/2008 | Alonso Fernandez et al. |
| 2010/0098794 | A1 | 4/2010 | Armand |
| 2011/0223151 | A1* | 9/2011 | Behrens ........... A61K 47/48246 424/94.64 |

FOREIGN PATENT DOCUMENTS

| | | |
|---|---|---|
| JP | 2007191396 A | 8/2007 |
| KR | 20150015209 | 2/2015 |
| RU | 2387341 C2 | 3/2010 |
| RU | 2524663 C1 | 7/2014 |
| TW | 201343190 A | 11/2013 |
| WO | 2005/116085 A1 | 12/2005 |
| WO | 2006/107825 A2 | 10/2006 |
| WO | 2008/003685 A1 | 1/2008 |
| WO | 2013/150193 A1 | 10/2013 |

OTHER PUBLICATIONS

Li, W., et al., Amphiphilically-modified gelatin nanoparticles: Self-assembly behavior, controlled biodegradability, and rapid cellular uptake for intracellular drug delivery, J. Mater. Chem., 2011, pp. 12381-12388.*
Kang, J., et al., "Cyclodextrin complexation: influence on the solubility, stability, and cytotoxicity of camptothecin, an antineoplastic agent", Eur. J. Pharm. Sci., 2002, pp. 163-170.*
Balthasar, S., et al., "Preparation and characterisation of antibody modified gelatin nanoparticles as drug carrier system for uptake in lymphocytes", Biomaterials, 2005, pp. 2723-2732.*
Asada, H., et al., "Absorption Characteristics of Chemical l y Modif ied-I nsu li n Derivatives with Various Fatty Acids in the Small and Large Intestine", J. Pharm. Sci., 2006, pp. 682-687.*
Aachmann, F.L., et al., "Structural background of cyclodextrin±protein interactions", Protein Engineering, 2004, pp. 905-912.*
Horsky. J.; Pitha J., "Inclusion Complexes of Proteins: Interaction of cyclodextrins with peptides containing aromatic aminoacids studied by competitives sepctrophotometry", Journal of Inclusion Phenomena and Molecula Recognition in Chemistry, vol. 18, N° 3, Netherlands, Sep. 1994, 291-300.
Fujimoto, M. et al., "Effect of heating process on the formation of nanoparticles of elastin model polypeptide, (GVGVP) 251, by gamma-ray crosslinking", Polymer Bulletin, Osaka, Japan, 2010, vol. 64, pp. 707-716.
Huh Kang Moo et al., "Supramolecular hydrogel formation based on inclusion complexation between PEG-modified chitosan and alpha-cyclodextrin", Macromolecular Bioscience, Ishikawa, Japan, Feb. 2004, vol. 4, No. 2, pp. 92-99.
Rinaudo M. et al., "Specific interactions in modified chitosan systems", Biomacromolecules, Ufa, Russia, vol. 6, No. 5, Sep. 2005, pp. 2396-2407.
Desbrieres J. et al., "Hydrophobic derivatives of chitosan: characterization and rheological behavior", International Journal of Biological Macromolecules, Elsevier, Grenoble, France, Jan. 1996, vol. 19, No. 1, pp. 21-28.
Galant Céline et al., "Altering associations in aqueous solutions of a hydrophobically modified alginate in the presence of beta-cyclodextrin monomers", The Journal of Physical Chemistry, Oslo, Norway, Jan. 2006, vol. 110, No. 1, pp. 190-195.
Burckbuchler Virginie et al., "Rheological and structural characterization of interactions between cyclodextrin compounds and hydrophobically modified alginate", Biomacromolecules, Oslo, Norway, Jun. 2006, vol. 7, No. 6, pp. 1871-1878.
Dowling M.B. et al, "A self-assembling hydrophobically modified chitosan capable of reversible hemostatic action", Biomaterials Elsevier Science, Baltimore, Maryland, May 2011, vol. 32, No. 13, pp. 3351-3357.
Karlberg M. et al., "Gels of hydrophobically modified hydroxyethylcellulose cross-linked by amylose. Competition with cyclodextrin", The ACS Journal of Surfaces and Colloids, Lund, Swedend, Feb. 2006, vol. 22, No. 5, pp. 2241-2248.
Sashiwa et al., "Chemical modification of chitosan. Synthesis of organosoluble, palladium adsorbable, and biodegradable chitosan derivatives toward the chemical plating on plastics", Biomacromolecules, Koyama, Tottori, Japan, Sep. 2002, vol. 3, No. 5, pp. 1120-1125.
Othman et al., "A comprehensive study of the spontaneous formation of nanoassemblies in water by a "lock-and-key" interaction between two associative polymers", Journal of Colloids and Interface Science, Chatenay-Malabry, France, Feb. 2011, vol. 354, No. 2, pp. 517-527.
Sihorkar V. et al., "Potential of polysaccharide anchored liposomes in drug delivery, targeting and immunization", Journal of Pharmacy and Pharmaceutrical Sciences, Sagar, India, Jul. 2001, vol. 4, No. 2, pp. 138-158.
Gilani, V. et al., "Development of respirable nanomicelle carriers for delivery of amphotericin B by jet nebulization", J. Pharm. Sciences, Tehran, Iran, vol. 100, No. 1, Jan. 2011, pp. 252-259.
Moazeni, E. et al., "Preparation and evaluation of inhalable itraconazole chitosan based polymeric micelles", DARU Journal of Pharmaceutical Sciences, Tehran, Iran, vol. 20, 85, Dec. 2012, pp. 1-9.
Song, S. et al., "Self-aggregated nanoparticles based on amphiphilic poly(lactic acid)-grafted-chitosan copolymer for ocular delivery of amphotericin B", Int. J. Nanomedicine, Chongqing, Republic of China, Sep. 2013, p. 3715.
Siew et al., "Enhanced oral absoprtion of hydrophobic and hydrophilic drugs using quaternary ammonium palmitoyl glycol chitosan nanoparticles", Molecular Pharmaceutics, Brunswick Square, London, vol. 9, No. 1, Jan. 2012, pp. 14-28.
Mannila et al., "Cyclodextrins and chitosan derivatives in sublingual delivery of low solubility peptides: A study using cyclosprin A, alpha-cyclodextrin and quaternary chitosan N-betainate", International Journal of Pharmaceutics, Kupio, Finland, vol. 381, No. 1, Oct. 2009, pp. 19-24.
Vieira, D.B. et al., "Cationic nanoparticles for delivery of amphotericin B: prepration, charcaterization and activity in vitro", J. Nanobiotech., Sao Paulo, Brazil, Jan. 2008, vol. 6, p. 6.
Albasarah et al., "Chitosan-coated antifungal formulations for nebulisation", J. Pharmacy Pharmacol., London, United Kingdom, vol. 62, No. 7, Jul. 2010, pp. 821-828.
Gharib, A. et al., "Preparation and antifungal activity of spray-dried amphotericin B-loaded nanospheres", DARU, Tehran, Iran, vol. 19, No. 5, Jun. 2011, pp. 351-355.
Odds F.C., "Synergy, antagonism, and what the chequerboard puts betwwen them", J. Antimicrobial Chemotherapy, Aberdeen, United Kingdom, vol. 52, No. 1, Jul. 2003, p. 1.
Huang, M. et al., "Uptake and cytotoxicity of chitosan molecules and nanoparticles : effects of molecular weight and degree of deacylation", Pharmaceutical Research, Singapore, Singapore, vol. 21, No. 2, Feb. 2004, pp. 344-353.
Bravo-Osuna, I. et al., "Mucoadhesion mechanism of chitosan and thiolated chitosan-poly(isobutyl cyanoacruylate) core-shell nanoparticles", Biomaterials, Chatenay-Malabry, France, vol. 28, No. 13, Apr. 2007, pp. 2233-2243.
Saint-Pierre-Chazalet, M. et al., "Membrane sterol depletion impairs action in wild-type and miltefosine-resistant Leishmania donovani promastigotes", J. Antimicrob. Chemother., Bobigny, France, Nov. 2009, vol. 64, No. 5, pp. 993-1001.
Owen, D.H. and Katz, D.F., "A vaginal fluid stimulant", Contraception, Durham, North Carolina, USA, Feb. 1999, vol. 59, No. 2, pp. 91-95.
Audisio, D. et al., "Synthesis and antikinetoplastid activities of 3-substituted quinolinones derivatives", Eur. J. Med. Chem., Chatenay-Malabry, France, Jun. 2012, vol. 52, pp. 44-50.
Bravo-Osuna, I. et al, "Elaboration and characterization of thiolated chitosan-coated acrylic nanoparticles", Int. J. Pharm, Chatenay-Malabry, France, vol. 316, Issues 1-2, Apr. 2006, pp. 170-175.
Camuzat-Dedenis B. et al., "Synthesis and in vitro trichomonacidal activities of some new dialkylperoxides and 1,2,4-trioxanes", Eur. J. Med. Chem., Chatenay-Malabry, France, vol. 36, No. 10, Oct. 2001, pp. 837-842.

(56) References Cited

OTHER PUBLICATIONS

Fujimoto, M. et al., "Preparation of alpha-elastin nanoparticles by gamma irradiation", Radiation Physics and Chemistry, 2009, vol. 78, Issue 12, pp. 1046-1048.
Teglia, A. et al., "New protein ingredients for skin detergency: native wheat protein-surfactant complexes", Int. J. Cosmet. Sci., Tavernerio, Como, Italy, Dec. 1994, vol. 16, No. 6, pp. 235-246.
Scheffel, U. et al., "Albumin microspheres for study of the reticuloendothelial system", J. Nucl. Med., Baltimore, Maryland, USA, Jul. 1972, vol. 13, No. 7, pp. 498-503.
Duclairor, C. et al., "Alpha-tocopherol encapsulation and in vitro release from wheat gliadin nanoparticles", Journal of Microencapsulation, Caen, France, Jan. 2002, vol. 19, No. 1, pp. 53-60.
Ezpeleta, I. et al.,"Gliadin nanoparticles for the controlled release of all-trans-retinoic acid", Int. J. Pham., Saint Etienne du Rouvray, France, 1996, vol. 131, pp. 191-200.
Veis, A., "The Macromolecular Chemistry of Gelatin", Journal of American Chemical Society, Academic Press. A. G. ,1964, New York, NY, p. 1824.
Li L-F et al: "Preparation and properties of protein films from stearic acid modified wheat gliadin", Gongneng Cailiao—Journal of Functional Materials, Gai-Kan Bianjibu, Chongqing, CN, vol. 39, No. 4, Apr. 1, 2008 (Apr. 1, 2008), pp. 656-659, abstract.

\* cited by examiner

SELF-ASSOCIATING MICROPARTICLES AND NANOPARTICLES CONSISTING OF PROTEINS

The invention relates to microparticles and nanoparticles comprised of proteins.

The invention also relates to the use thereof as an encapsulation system and the process for preparation of same.

Particles capable of encapsulating an active principle of interest or an active substance of interest are the subject of active research. Currently, microparticles and nanoparticles may be obtained by three large classes of processes: (i) physicochemical processes based on variations in the solubility of materials used for the encapsulation and on variations in temperature or pH, (ii) mechanical processes such as extrusion or thermal gelling, "hot-melt", and (iii) chemical processes in which synthesis of the polymer and encapsulation of active molecules are performed simultaneously.

Said particles must be capable of trapping an active substance of interest, transporting it into the organism to the cell or to the target tissue, then releasing it without any alteration of its structure. It is therefore important for these particles not to be toxic. However, because of the low solubility of certain proteins in water, the processes for preparation of said particles very often rely upon organic solvents in order to dissolve the proteins. These processes also have other disadvantages. In fact, they often require, during at least one step, the use of surfactants, the use of reagents, and even an extreme variation in pH. In some cases, it is also necessary to use heating or strong agitation, which cause a loss of energy and increase the time and cost of production.

The active substance of interest may thus undergo degradation due to the solvents, surfactants and reagents used, or the agitation or heating necessary for producing particles. These conditions may also be the cause of therapeutic inefficacy of the particles obtained.

In addition, the majority of processes leading to the formation of protein-based particles are performed in multiple steps, thereby also increasing the time and cost of production.

This is the case, for example, of the preparation of particles by solvent emulsion-diffusion.

Similarly, additional steps for purifying the preparations and removing excess reagents, solvents or surfactants are often necessary after production.

None of the processes mentioned above is therefore satisfactory, and therefore a new process for producing particles comprised of proteins is desired.

Proteins are widely used in the pharmaceutical field or in the cosmetic field, in particular for encapsulation of active substances of interest. Among the proteins commonly used, gliadin and gelatin are advantageous owing to their mucoadhesive properties.

Gliadin is a protein obtained from wheat, comprised of a polypeptide chain having a molar mass capable of varying between 25 and 100 kDa, characterized by the presence of disulfide bridges. Gliadin may interact with keratin at the level of the epidermis (Teglia, A. and Secchi, G., Int. J. Costa. Sci. 16 (1994) 235-246). This protein has, for example, been used for the oral administration of active molecules, such as clarithromycin, omeprazole (Ramteke & Jain, Journal of Drug Targeting. 2008, 16(1), 65-72), and α-tocopherol (Duclairor et al., Journal of Microencapsulation, 2002, 19(1), 53-60). The methods currently used to prepare said particles nevertheless rely upon organic solvents, in particular ethanol, since this protein has very low water solubility (Ezpeleta, I. et al., 1996. Int. J. Pharm. 131, 191-200).

In general, gelatin has a number-average molecular mass (Mn) of between 50 Da and 100 kDa, and a weight-average molecular mass (Mw) of between 100 Da and 1000 kDa, with a polydispersity index Ip (Mw/Mn) often higher than 2, due to the heterogeneity of the gelatin (Wiley, Gelatin Handbook). Gelatin is obtained by partial hydrolysis of collagen (Harding, J. J. (1965). The unusual links and cross-links of collagen. Advances in Protein Chemistry, 20, 109-190, Veis, A. (1964). The macromolecular chemistry of gelatin. Academic Press: London, Ward, A. G., & Courts, A. (1977). The science and technology of gelatin. London: Academic Press). Collagen is extracted from skin, for example pig skin, bones and cartilage.

Scheffel U et al., (1972, J Nucl Med, July; 13(7):498-503), describes the preparation of albumin nanoparticles by different methods such as emulsification, which requires a large supply of energy and an increase in temperature.

Elastin is also a protein very often used, in particular in the cosmetic field. It has a very dense structure that renders it insoluble in water. Studies have nevertheless been conducted in order to demonstrate that there is a possibility of modifying elastin in order to render it more soluble in water (U.S. Pat. No. 4,363,760).

The U.S. Pat. No. 4,659,740 describes the use in the cosmetic field of elastin derivatives grafted by fatty acids (such as lauric acid, palmitic acid or oleic acid) forming amide bonds, by transformation of the acid into anhydride capable of reacting with the amine groups of the elastin. This formulation has made it possible to have a better penetration of the elastin through the skin, in particular a better absorption at the level of the stratum corneum.

The use of alpha-elastin derivatives capable of auto-associating in an aqueous medium has also been described. The particles obtained were cross-linked by gamma radiation in order to solidify them (Fujimoto et al, Radiation Physics and Chemistry, 2009, 78, 1046-1048). Nanoparticles having a size of 150 nm and 300 nm were obtained (Fujimoto et al., Polymer Bulletin, 2010, 64, 707-716).

The international application WO/2005/116085 also describes the association between a cyclodextrin to which an organofunctional group is bound and a hydrolyzed protein.

One of the objectives of the invention is therefore that of providing inclusion complexes between a hydrophobized protein and a cyclodextrin.

One of the other objectives of the invention is that of providing particles formed from said inclusion complexes.

One of the other objectives of the invention is that of providing a simple process for preparation of said particles without the systematic use of solvents, surfactants or reagents.

One of the other objectives of the invention is that of providing a process for preparing said particles not requiring a significant increase in temperature or strong agitation of the preparation.

The invention also relates to the use of said particles, as well as compositions containing said particles.

The invention also relates to an encapsulation system containing said particles, as well as a process for preparing said encapsulation system.

The invention thus relates to an inclusion complex formed by the interaction between:
at least one protein comprising hydrophobic groups covalently bound to said protein, and at least one α-cyclodextrin (CD) in the form of a monomer,
the protein and the cyclodextrin being non-covalently bound.

The term "inclusion complex" designates a system consisting of a host molecule capable of receiving a chemical species.

The term "protein" designates a biological macromolecule comprised of one or more amino acid chains bound to one another by peptide bonds Amino acids are a class of chemical compounds of formula $H_2N—CHR—COOH$. Each amino acid therefore has an amine group $—NH_2$, a carboxyl group —COOH, and an R group, which represents the side chain that identifies the amino acid, (for example, $CH_2—SH$ for cysteine, $CH_2—OH$ for serine, H for glycine . . . ).

The expression "protein comprising hydrophobic groups" means that the protein has been hydrophobized by grafting, on amino groups and/or carboxyl groups and/or hydroxyl groups and/or thiol groups, of alkyl chains that are, by nature, hydrophobic owing to their apolar character. The proteins grafted by hydrophobic chains are amphiphilic systems capable of being spontaneously auto-associated in an aqueous medium in the form of core-crown micelles capable of receiving an active principle. The proteins are in particular grafted by lipid groups. These systems have demonstrated high stability over time. The solubility of said proteins in an aqueous medium decreases, however, due to the presence of grafted hydrophobic chains.

A cyclodextrin (or cycloamylose) is a cyclic oligosaccharide of β-D-glucopyranose linked by α(1-4) bonds. This is a cage molecule of natural origin that makes it possible to encapsulate various molecules, in particular molecules of therapeutic interest. There are different sizes (α, β, γ), each having a "lampshade" shape. It has —OH hydrophilic groups located outside, the whole defining a relatively hydrophobic cavity. This amphiphilic character enables the cyclodextrin to include, in its cavity, hydrophobic molecules for forming water-soluble inclusion complexes. Its biodegradable character predisposes it to significant applications in the agrifood and pharmaceutical fields. The encapsulation in cyclodextrins in fact makes it possible to protect fragile molecules or ensure their slow and controlled release.

In this invention, the term "cyclodextrin" designates only α-cyclodextrin.

The expression "in the form of a monomer" means that only one cyclodextrin unit is present. The use of alpha-cyclodextrin in the form of a monomer instead of a cyclodextrin polymer has an obvious advantage from an economical and regulatory point of view because said cyclodextrin is available on the market and is recognized as being a pharmaceutical excipient accepted by most pharmacopeia.

The expression "the protein and the cyclodextrin being non-covalently bound" means that the interactions between said molecules are of the Van der Waals and/or hydrogen and/or hydrophobic and/or electrostatic type, and not covalent bonds.

The inclusion complexes according to the invention are thus formed exclusively by non-covalent bonds simply by mixing α-cyclodextrin and protein grafted by hydrophobic groups. Using the same procedure and varying the type of said non-covalent interactions, it is then possible to form particles of various sizes and structures.

Advantageously, in the inclusion complex according to the invention, the protein has a molar mass of between 100 Da to 1,000,000 kDa, and in particular from 10 to 100 kDa.

Advantageously, in the inclusion complex according to the invention, the ratio between the cyclodextrin concentration in g/L and that of the protein is between $10^{-6}$ and 900,000.

Also advantageously, in the inclusion complex according to the invention, the ratio between the cyclodextrin concentration in g/L and that of the protein is between 0.01 and 1500, in particular between 4 and 15 and in particular equal to 10.

According to another aspect, the invention relates to an inclusion complex formed by the interaction between:
  an association of proteins comprising hydrophobic groups covalently bound to said protein, and
  at least one α-cyclodextrin (CD) in the form of a monomer,
the protein and the cyclodextrin being non-covalently bound.

The expression "association of proteins" means that at least two different proteins are present in the inclusion complex, for example, gelatin and gliadin.

The invention relates in particular to an inclusion complex in which the protein is chosen from elastin, collagen, gliadin, gelatin, keratin, albumin, legumin, vicilin, casein, fibrinogen, insulin, fibrinonectin, a hormone, an enzyme, a coagulation factor, transferrin, fibrillin, an immunoglobulin, a cereal protein (wheat, rice, . . . ), a protein obtained from grains or nuts, a protein obtained from algae, a silk protein, an egg protein, a potato protein, and derivatives of said proteins, and is, in particular, gliadin or gelatin.

According to a particular embodiment of the invention, in the inclusion complex according to the invention, the degree of substitution of the protein by hydrophobic groups is between 0.001 and 100%.

Advantageously, in the inclusion complex according to the invention, the degree of substitution of the protein by the hydrophobic groups is between 0.005 and 50%.

The degree of substitution is also a parameter making it possible to modulate the average size of the particles formed from inclusion complexes.

The rate of grafting of the protein by the hydrophobic groups may be calculated by using different analytical methods such as elementary analysis and NMR spectroscopy of the proton of the grafted protein.

The invention relates in particular to an inclusion complex formed by the interaction between:
  at least one protein comprising hydrophobic groups covalently bound to said protein, and
  at least one α-cyclodextrin (CD) in the form of a monomer,
the protein and the cyclodextrin being non-covalently bound,
  in particular in which the protein is chosen from elastin, collagen, gliadin, gelatin, keratin, albumin, legumin, vicilin, casein, fibrinogen, insulin, fibrinonectin, a hormone, an enzyme, a coagulation factor, transferrin, fibrillin, an immunoglobulin, a cereal protein (wheat, rice, . . . ), a protein obtained from grains or nuts, a protein obtained from algae, a silk protein, an egg protein, a potato protein, and derivatives of said proteins, and is, in particular, gliadin or gelatin,
  in which the hydrophobic groups are alkyl groups, linear or branched, in particular linear, containing 1 to 1000 carbon atoms, in particular 2 to 20, or alkenyl groups, linear or branched, in particular linear, containing 2 to 1000 carbon atoms, in particular 2 to 20, containing at least one double bond C═C, conjugated or not, and in particular lipid hydrophobic groups, in particular palmitic acid, oleic acid, lauric acid, stearic acid and/or linoleic acid.

According to an advantageous embodiment, in the inclusion complex of the invention, the hydrophobic groups are alkyl groups, linear or branched, in particular linear, containing 6 to 100 carbon atoms, or alkenyl groups, linear or branched, in particular linear, containing 6 to 100 carbon atoms.

Palmitic acid, oleic acid, lauric acid, stearic acid and/or linoleic acid are in particular used for grafting hydrophobic chains on the protein, but this list is in no way exhaustive and limiting.

| Fatty acid | Formula |
|---|---|
| Lauric acid (12:0) | ![structure] |
| Palmitic acid (16:0) | ![structure] |
| Stearic acid (18:0) | ![structure] |
| Linoleic acid (18:2 Δ9, 12) | ![structure] |
| Oleic acid (18:1 Δ9) | ![structure] |

According to another particular embodiment, in the inclusion complex of the invention, the hydrophobic groups are alkyl groups, linear or branched, in particular linear, containing 1 to 1000 carbon atoms, in particular 2 to 20, or alkenyl groups, linear or branched, in particular linear, containing 2 to 1000 carbon atoms, in particular 2 to 20, and having 1 to 4 double bonds C=C, conjugated or not.

According to another particular embodiment of the invention, in the inclusion complex of the invention, the hydrophobic groups are covalently bound to the protein by the amine function and/or the carboxyl function and/or the hydroxyl function and/or the thiol function.

Said hydrophobic groups are thus fixed by an N-acylation and/or O-acylation and/or S-acylation reaction with a fatty acid or a fatty acid derivative such as a fatty acid chloride (palmitic acid chloride or oleic acid chloride, for example).

General Procedure

The hydrophobization of the proteins may be performed by dissolving the protein, then by heating the mixture to 90° C. under continuous magnetic agitation. The fatty acid chloride, for example, palmitoyl chloride, is then added. The mixture is left at 90° C. for several hours, then left at ambient temperature. The acylated protein is then precipitated, collected, washed and then dried.

After acylation, on the IR spectrum of the acylated protein, the presence of bands corresponding to the alkyl chains of the fatty acid must be observed, in comparison with the IR spectrum of the native protein.

Said hydrophobization may be performed in a solvent if the protein is soluble in the latter and if it is sought to graft the protein with an acid chloride (the acid chloride is hydrolyzed in the presence of water). It is also possible not to use solvent, and to perform the hydrophobization only in the presence of water, on the condition that the protein is water-soluble and on the condition that other grafting methods are used, such as those with acid anhydride (see U.S. Pat. No. 4,659,740, for example).

In the sense of this invention, "solvent" thus designates any solvent with the exception of water or an aqueous medium.

According to another embodiment, in the inclusion complex of the invention, cyclodextrin (CD) has the formula:

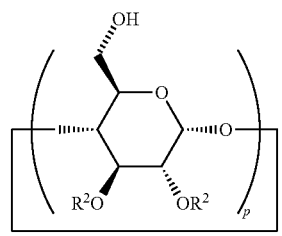

wherein
p is an integer equal to 6,
R1, R2, R3, identical or different, in particular identical, are hydrogen atoms, alkyl groups comprising 1 to 3 carbon atoms, chosen from methyls, ethyls, propyls, isopropyls, amino groups —$NH_2$, ammonium groups —$NH_3^+$, or sulfate groups —$SO_4^{2-}$, and are in particular hydrogen atoms or methyl groups,
said CD being in the form of a monomer,
and in particular in which the cyclodextrin is functionalized by a ligand chosen from antibodies, antibody fragments, receptors, lectins, biotin or derivatives thereof The α-cyclodextrin is schematically represented below:

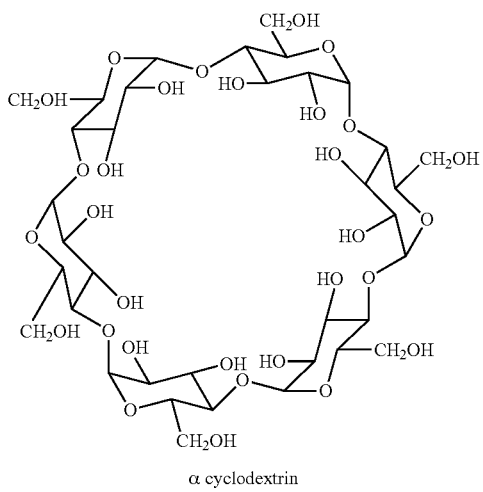 [SMILES: OCC1OC2OC3C(CO)OC(OC4C(CO)OC(OC5C(CO)OC(OC6C(CO)OC(OC7C(CO)OC(OC1C(O)C2O)C(O)C7O)C(O)C6O)C(O)C5O)C(O)C4O)C(O)C3O]

α cyclodextrin

Its geometry is comparable to a cone trunk defining a cavity at its center. It is described in FIG. 10. It is therefore a cage molecule, capable of receiving chemical species by an inclusion phenomenon, in particular molecular and hydrophobic species. The internal part of the cavity is hydrophobic, and the external part is hydrophilic.

The —OH groups may be substituted, in particular by methyl, hydroxypropyl or sulfobutyl groups. The substitutions may increase the solubility of cyclodextrin.

The advantage of α-cyclodextrin is its small size, which enables it to interact with the hydrophobic chains linked to the protein.

According to a particular embodiment, the cyclodextrin is functionalized by a ligand chosen from antibodies, antibody fragments, receptors, lectins, biotin or derivatives thereof The term "ligand" designates a molecule capable of binding covalently to cyclodextrin. The ligand is chosen from protein compounds involved in particular in the recognition and/or neutralization of pathogenic agents (antibodies or fragments, receptors, lectins), involved in the metabolism of fatty acids (biotin and derivatives).

According to another particular aspect, in the inclusion complex of the invention, the cyclodextrin is charged or uncharged.

According to yet another aspect, in the inclusion complex of the invention, the cyclodextrin is substituted or unsubstituted.

The term "substituted cyclodextrin" refers, for example, to a cyclodextrin substituted by an alkyl group, for example a methylated cyclodextrin, by a hydroxyalkyl group, by a maltosyl group, by a galactosyl group, or by any other molecule.

According to another aspect, the invention relates to an inclusion complex, in which the protein is functionalized by a ligand chosen from antibodies, antibody fragments, receptors, lectins, biotin or derivatives thereof According to another particular aspect, the invention relates to an inclusion complex, in which the protein is gliadin bearing hydrophobic groups fixed by the amine function and/or the carboxyl function and/or the hydroxyl function and/or the thiol function, and representing groups of formula:

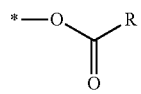

and/or

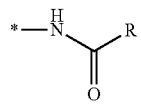

and/or

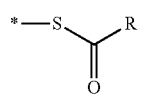

and/or

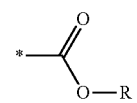

wherein
* represents the protein,
R represents the hydrophobic group and is chosen from:
an alkyl group, linear or branched, containing 1 to 1000 carbon atoms, in particular the groups —(CH$_2$)$_{14}$—CH$_3$ or —(CH$_2$)$_{16}$—CH$_3$,
an alkenyl group, linear or branched, containing 2 to 1000 carbon atoms and containing at least one double bond C=C, in particular the groups —(CH$_2$)$_7$—CH=CH=CH$_2$—(CH$_2$)$_7$—CH$_3$ or —(CH$_2$)$_7$—CH=CH—(CH$_2$)$_7$—CH$_3$.

According to another particular aspect, the invention relates to an inclusion complex, in which the protein is gelatin bearing hydrophobic groups fixed by the amine function and/or the carboxyl function and/or the hydroxyl function and/or the thiol function, and representing groups of formula:

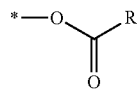

and/or

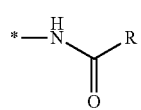

and/or

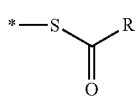

and/or

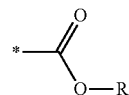

wherein
* represents the protein,
R represents the hydrophobic group and is chosen from:
an alkyl group, linear or branched, containing 1 to 1000 carbon atoms, in particular the groups —$(CH_2)_{14}$—$CH_3$ or —$(CH_2)_{16}$—$CH_3$,
an alkenyl group, linear or branched, containing 2 to 1000 carbon atoms and containing at least one double bond C=C, in particular the groups —$(CH_2)_7$—CH=CH=$CH_2$—$(CH_2)_7$—$CH_3$ or —$(CH_2)_7$—CH=CH—$(CH_2)_7$—$CH_3$.

From the inclusion complexes according to the present invention, it is possible to form particles. Said particles in fact contain an association of a plurality of inclusion complexes.

Another aspect of the invention then relates to a particle having a size of between 1 nm and 100,000 nm, in particular 200 nm to 8000 nm, containing inclusion complexes between:
at least one protein comprising hydrophobic groups covalently bound to said protein, and
at least one α-cyclodextrin (CD) in the form of a monomer.

The invention thus relates to nanometric particles, having a size of between 1 nm and 1000 nm, and micrometric particles, having a size of between 1000 nm and 100 000 nm.

The size of the particles formed was evaluated by quasi-elastic light scattering (QUELS) and by transmission electron microscopy (TEM).

The size plays a very important role concerning the quantity of active principle encapsulated and the applications envisaged, and the route of administration of the active principle.

According to a particular aspect, the invention relates to a particle in which the protein has a molar mass of between 100 Da and 1,000,000 kDa, and in particular 10 to 100 kDa, said protein being chosen in particular from elastin, collagen, gliadin, gelatin, keratin, albumin, legumin, vicilin, casein, fibrinogen, insulin, fibrinonectin, a hormone, an enzyme, a coagulation factor, transferrin, fibrillin, an immunoglobulin, a cereal protein (wheat, rice, . . . ), a protein obtained from grains or nuts, a protein obtained from algae, a silk protein, an egg protein, a potato protein, and derivatives of said proteins, and is, in particular, gliadin or gelatin.

According to yet another aspect, the invention relates to a particle in which said protein and/or said α-cyclodextrin (CD) are functionalized by a ligand chosen from antibodies, antibody fragments, receptors, lectins, biotin or derivatives thereof.

According to yet another aspect, the invention relates to a particle containing inclusion complexes in which the ratio between the cyclodextrin concentration in g/L and that of the protein, in particular gliadin or gelatin, is between de $10^{-6}$ and 900,000.

According to yet another aspect, the invention relates to a particle containing inclusion complexes in which the ratio between the cyclodextrin concentration in g/L and that of the protein, in particular gliadin or gelatin, is between 0.01 and 1500, in particular between 4 and 15, and in particular equal to 10.

The ratio between the cyclodextrin concentration in g/L and that of the protein is a very important parameter because it makes it possible to modulate the size of the particles obtained from the above-mentioned inclusion complexes, by modifying the ratio of concentration between the cyclodextrin and the protein.

According to another aspect, the invention relates to a particle containing inclusion complexes in which the degree of substitution of the protein by the hydrophobic groups is between 0.001 and 100%, in particular from 0.005 to 50%.

According to yet another aspect, the invention relates to a particle containing inclusion complexes in which the hydrophobic groups are alkyl groups, linear or branched, in particular linear, containing 1 to 1000 carbon atoms, in particular 2 to 20, or alkenyl groups, linear or branched, in particular linear, containing 2 to 1000 carbon atoms, in particular 2 to 20, containing at least one double bond C=C, conjugated or not, and in particular lipid hydrophobic groups, in particular palmitic acid, oleic acid, lauric acid, stearic acid and/or linoleic acid.

According to yet another aspect, the invention relates to a particle containing inclusion complexes in which the hydrophobic groups are covalently fixed to the protein by the amine function and/or the carboxyl function and/or the hydroxyl function and/or the thiol function.

According to yet another aspect, the invention relates to a particle containing inclusion complexes formed by the interaction of an association of proteins and at least one α-cyclodextrin (CD).

The proteins contained in the inclusion complexes according to the invention may also be used to encapsulate active substances of interest.

In yet another aspect, the invention thus relates to an encapsulation system containing one or more above-mentioned particles, and one or more active substance(s) of interest used for their properties in the pharmaceutical, medical, paramedical, medical device, cosmetics, veterinary, agrifood, animal feed, agrochemistry, pesticide, cosmetotextile, perfumery or environmental fields, or in the paint, construction and/or automobile industry.

The term "encapsulation system" thus means that a protein forming an inclusion complex according to this invention may itself be the host of one or more active substance(s) of interest.

According to an advantageous aspect, the active substance of interest has pharmaceutical properties and is chosen from synthetic or natural inorganic and organic compounds.

The encapsulation system defined above may be used to prepare suitable compositions in the pharmaceutical, medical, paramedical medical device, cosmetics, veterinary, agrifood, animal feed, agrochemistry, pesticide, cosmetotextile, perfumery or environmental fields, or in the paint, construction and/or automobile industry.

The encapsulated active substance of interest may have pharmaceutical properties and be an active principle for therapeutic use. It may belong to the following list, which is in no way limiting, to the group of compounds with properties of vitamins, in particular vitamin A, vitamin E, vitamin C, the K vitamins, the B vitamins, vitamin D, anti-tumor drugs, in particular paclitaxel, docetaxel, tamoxifen, doxorubicin, anti-pain drugs, in particular paracetamol, anti-inflammatories, in particular diclofenac, ibuprofen, ketoprofen, antibiotics, in particular penicillins, tetracyclins, antifungals, in particular ketoconazole, clotrimazole, nystatin, chlorhexidine and derivatives thereof, antiparasitics, in particular albendazole, metronidazole, enzymatic agents, in particular alkaline phosphatase, acetylcholinesterase, alcohol dehydrogenase, hormonal agents, in particular testosterone, levonorgestrel, anxiolytics, in particular benzodiazepines, antidiabetics, in particular gliclazide, antihypertensive properties, in particular nifedipine, or vaccines, antivirals, in particular AZT, analgesics or combinations of analgesics, in particular paracetamol, antiepileptics, in particular barbiturates and derivatives, local and general anesthetics, in particular atropine, but also hypnotics, sedatives, antipsychotics, neuroleptics, antidepressants, anxiolytics, in particular antagonists, nerve blocks, anticholinergics, cholinomimetics, antimuscarinics, muscarinics, in particular anti-adrenergics, antiarrhythmics, antiarthritics, antiasthmatics, anticonvulsants, antihistamines, anti-nausea drugs, antineoplastics, antipyretics, antipruritcs, antispasmodics, vasodilators, central nervous system stimulants, in particular cough and cold preparations, decongestants, bone growth stimulants, bone resorption inhibitors, immunosuppressants, muscle relaxants, psychostimulants, sedatives, tranquilizers, proteins, peptides or fragments thereof, said proteins, peptides or fragments being natural, recombinant or chemically produced products, nucleic acids (ribonucleotides or deoxyribonucleotides), in particular single and double-strand molecules, gene constructs, expression vectors, anti-sense molecules and the like.

Said active substance of interest for therapeutic use may be used in humans and in animals.

The encapsulated active substance of interest may also have cosmetic properties and belong to the group of compounds with ant-inflammatory, anti-aging, anti-ultraviolet (anti-UV), depigmenting, cicatrization, hydrating, fragrance, deodorizing, antibacterial, antitranspirant, cleaning, coloring or preservative properties.

In one particular encapsulation system, the active substance of interest has dietary properties and belongs to the group of compounds with vitamin, enzymatic and sweetening properties. It may also be an essential oil, a coloring agent, a preservative, an antioxidant or a probiotic.

Some molecules or families of molecules capable of being encapsulated as active substances of interest are: molsidomine, ketoconazole, gliclazide, diclofenac, levonorgestrel, paclitaxel, docetaxel, tamoxifen, hydrocortisone, pancratistatin, ketoprofen, diazepam, ibuprofen, nifedipine, testosterone, tamoxifen, furosemide, tolbutamide, chloramphenicol, benzodiazepines, naproxen, dexamethasone, diflunisal, anadamide, pilocarpine, daunorubicin, doxorubicin, essential oils, terpenes and terpenoids.

To improve the solubility of said molecules, it is possible to use a solvent or a mixture of solvents, in particular: alkyl acetate (ethyl acetate, butyl acetate, methyl acetate), acetone, acetonitrile, acetic acid, methanoic acid, ammoniac, acetic anhydride, aniline, anisole, benzene, butanol, butanone, chlorobenzene, chloroform, cyclohexane, cyclopentane, dichloroethane, dichloromethane, diisopropyl ether, dimethylformamide, dimethylsulfoxide, dioxane, ethanol, glycol ether, diethyl ether, ethylene glycol, heptane, hexamethylphosphoramide, hexane, methanol, methyl ethyl ketone, nitrobenzene, pentane, perchloroethylene, propanol, propoxypropane, pyridine, carbon sulfide, tetrachloroethane, tetrahydrofuran, toluene, trichloroethane, trichloroethylene, trimethylpentane, xylene.

Said solvent or solvent mixture is added before adding the cyclodextrin and the hydrophobized protein.

In yet another aspect, the invention relates to a pharmaceutical composition containing, as an active substance of interest, a substance encapsulated in inclusion complexes as mentioned above or in the above-mentioned particles, in the form of a solid, or in the form of a solution or in the form of a suspension in an aqueous medium such as pure water, an aqueous solution comprising one or more solutes, in particular one or more salt(s) and/or sugar(s), in particular saccharose or glucose, an injectable solution or a suspension or a physiological serum solution optionally enriched with glucose, an emulsion, a gel, a cream, or any other pharmaceutically acceptable excipient.

According to a particular aspect, the invention relates to a pharmaceutical composition, said composition being capable of being used by the following routes:

parenteral, intravenous, oral, buccal, sublingual, cutaneous, subcutaneous, nasal, rectal, vaginal, pulmonary, or ocular and for any administration at a mucous membrane, or at a specific site (tumor, opening of certain blood vessels), in the form of a tablet, a soft capsule, a hard capsule, a powder, a granule, chewing gum, toothpaste, subgingival irrigations, dental or oral pre-brushing solutions, a patch, an implant, a suppository, a solution, a suspension, a syrup, a paste, a cream, a gel, an emulsion, a spray, a lotion, a pomade, a nail polish, a hairspray or a shampoo.

The advantageous forms in the pharmaceutical field are tablets, soft capsules, hard capsules, powders, granules, patches, implants, suppositories, solutions, suspensions, syrups, pastes, creams, gels, emulsions, sprays, lotions, pomades, nail polishes and hairsprays.

The advantageous forms in the paramedical field are dressings, catheters, compresses, gauze, hydrophilic cotton, physiological serum, sprays . . . .

The advantageous forms in the field of medical devices are implants, prostheses, instrument washes-disinfectants, compresses, dressings (in particular for cicatrization), sprays, gauzes, hydrophilic cotton . . . .

The advantageous forms in the veterinary field are oral forms (tablets, powders, soft capsules, hard capsules, granules, pastes, solutions, suspensions), injectable agents (solutions, suspensions, emulsions) and topical agents, the action of which may be local or systemic (spray, collars, ear tags, powders, lotions, pomades, shampoos, patches, emulsions, milk, gel, cream, nail polish, hairspray).

The advantageous forms in the dietary field are solutions, emulsions, pastes, gels, powders used alone or included in food preparation; in the field of dietary supplements: primarily oral forms (powders, tablets, capsules, granules, soft capsules or hard capsules, pastes, solutions, suspensions, infusions or emulsions).

According to a particular aspect, the invention relates to a cosmetic composition containing, as an active substance of interest, a substance encapsulated in inclusion complexes as mentioned above or in the aforementioned particles, in solid form, in the form of a solution or in the form of a suspension in an aqueous medium such as pure water, an aqueous solution including one or more solutes, in particular one or more salt(s) and/or polymer(s), and/or surfactants, in particular polysorbate 80 or sodium laurylsulfate, an emulsion, a gel, a cream, or any other cosmetically acceptable excipient.

According to a particular aspect, the invention relates to a cosmetic composition, said composition being capable of being used orally, cutaneously, on the nails, on the hair, in the form of a tablet, a soft capsule, a hard capsule, a powder, a granule, a patch, an implant, a solution, a suspension, a paste, a cream, a gel, an emulsion, a spray, a lotion, a pomade, a nail polish, or a shampoo.

The invention also relates to a method for preparing an inclusion complex as defined above comprising a step of mixing at least:
- a protein comprising hydrophobic groups covalently bound to said protein, and
- an α-cyclodextrin (CD) in the form of a monomer, in order to obtain an inclusion complex in which said protein and said cyclodextrin are non-covalently bound.

According to a particular aspect, the invention relates to a method for preparing an inclusion complex as defined above, comprising a step of mixing at least:
- an association of proteins comprising hydrophobic groups covalently bound to said protein, and
- an α-cyclodextrin (CD) in the form of a monomer, in order to obtain an inclusion complex in which said protein and said cyclodextrin are non-covalently bound.

The use of multiple proteins may have the advantage of modulating the properties of particles by modifying the ratio between the proteins. It is thus expected that the size, the overall charge and the intended uses of said particles may be modulated.

According to another aspect, the invention relates to a preparation process comprising a step of mixing at least:
- one protein chosen from elastin, collagen, gliadin, gelatin, keratin, albumin, legumin, vicilin, casein, fibrinogen, insulin, fibronectin, a hormone, an enzyme, a coagulation factor, transferrin, fibrillin, an immunoglobulin, a cereal protein (wheat, rice, . . . ), a protein obtained from grains or nuts, a protein obtained from algae, a silk protein, an egg protein, a potato protein, and derivatives of said proteins, and is in particular gliadin or gelatin, said protein comprising hydrophobic groups of formula:

$$*-O-\underset{O}{\overset{}{\overset{\parallel}{C}}}-R$$

and/or $$*-\underset{}{\overset{H}{N}}-\underset{O}{\overset{}{\overset{\parallel}{C}}}-R$$

and/or $$*-S-\underset{O}{\overset{}{\overset{\parallel}{C}}}-R$$

and/or $$*-\underset{O}{\overset{}{\overset{\parallel}{C}}}-O-R$$

wherein
* represents the protein,
R represents the hydrophobic group and is chosen from:
- an alkyl group, linear or branched, containing 1 to 1000 carbon atoms, in particular the groups —(CH$_2$)$_{14}$—CH$_3$ or —(CH$_2$)$_{16}$—CH$_3$,
- an alkenyl group, linear or branched, containing 2 to 1000 carbon atoms and containing at least one double bond C═C, in particular groups —(CH$_2$)$_7$—CH═CH—CH$_2$—(CH$_2$)$_7$—CH$_3$ or —(CH$_2$)$_7$—CH═CH—(CH$_2$)$_7$—CH$_3$, and an α-cyclodextrin (CD) having, as its formula:

[chemical structure of α-cyclodextrin monomer unit with OR$^2$ groups, repeated p times]

wherein
p is an integer equal to 6,
R1, R2, R3, identical or different, in particular identical, are hydrogen atoms, alkyl groups comprising 1 to 3 carbon atoms, chosen from methyls, ethyls, propyls, isopropyls, amino groups —NH$_2$, ammonium groups —NH$_3^+$, or sulfate groups —SO$_4^{2-}$, and are in particular hydrogen atoms or methyl groups,
said CD being in the form of a monomer,
in particular in which said protein and said α-cyclodextrin (CD) are functionalized by a ligand chosen from antibodies, antibody fragments, receptors, lectins, biotin or derivatives thereof in order to obtain an inclusion complex in which said protein and said cyclodextrin are non-covalently bound.

In yet another aspect, the invention relates to a preparation process in which the mixture is produced at ambient temperature.

In the method for preparing an inclusion complex according to this invention, the protein may be in solution in an aqueous medium or in the form of a suspension in an aqueous medium.

In the method for preparing an inclusion complex according to this invention, the cyclodextrin may be in solution in an aqueous medium or in the form of a suspension in an aqueous medium.

The term "aqueous medium" refers in particular in the sense of this invention to pure water, an aqueous solution comprising one or more solutes, in particular one or more salt(s) and/or sugar(s), in particular saccharose or glucose, an injectable solution or suspension or a physiological serum solution, optionally enriched with glucose, an emulsion, a gel, a cream, or any other pharmaceutically acceptable excipient.

According to a particular aspect, the invention relates to a preparation process in which:
said protein is in the form of a suspension in an aqueous medium, said α-cyclodextrin (CD) is, preferably, in solution in an aqueous medium,
said aqueous medium being chosen from pure water, an aqueous solution having a pH of between 1 and 14, in particular between 5 and 8, comprising one or more solutes, in particular one or more salt(s) and/or sugar(s), in particular saccharose or glucose, an injectable solution or suspension, a physiological serum solution, optionally enriched with glucose, an emulsion, a gel, a cream, or any other excipient for pharmaceutical, cosmetic, agrifood or veterinary use.

The term "injectable solution" refers in particular in the sense of this invention to water for injectable preparations, a sodium chloride solution, or a sodium-based solution.

According to another particular aspect, the invention relates to a preparation process in which
said protein is in solution in an aqueous medium,
said α-cyclodextrin (CD) is preferably in solution in an aqueous medium,
said aqueous medium being chosen from pure water, an aqueous solution having a pH of between 1 and 14, in particular between 5 and 8, comprising one or more solutes, in particular one or more salt(s) and/or sugar(s), in particular saccharose or glucose, an injectable solution or suspension, a physiological serum solution, optionally enriched with glucose, an emulsion, a gel, a cream, or any other excipient for pharmaceutical, cosmetic, agrifood or veterinary use.

According to yet another particular aspect, the invention relates to a preparation process in which
said protein is in solution in an aqueous medium,
said α-cyclodextrin (CD) is preferably in solution in an aqueous medium,
said aqueous medium being chosen from pure water, an aqueous solution having a pH of between 1 and 14, in particular between 5 and 8, including one or more solutes, in particular one or more salt(s) and/or sugar(s), in particular saccharose or glucose, an injectable solution or suspension, a physiological serum solution, optionally enriched with glucose, an emulsion, a gel, a cream, or any other excipient for pharmaceutical, cosmetic, agrifood or veterinary use.

According to yet another aspect, the invention relates to a preparation process in which
said protein is in the form of a suspension in an aqueous medium,
said α-cyclodextrin (CD) is preferably in the form of a suspension in an aqueous medium,
said aqueous medium being chosen from pure water, an aqueous solution having a pH of between 1 and 14, in particular between 5 and 8, comprising one or more solutes, in particular one or more salt(s) and/or sugar(s), in particular saccharose or glucose, an injectable solution or suspension, a physiological serum solution, optionally enriched with glucose, an emulsion, a gel, a cream, or any other excipient for pharmaceutical, cosmetic, agrifood or veterinary use.

According to another particular aspect, the invention relates to a preparation process, said process comprising, prior to the mixing step, a step of preparing a protein having hydrophobic groups, by an N-acylation and/or O-acylation and/or S-acylation reaction between said protein and 0.1 to 100 equivalents per unit of protein, of fatty acid chloride having the formula

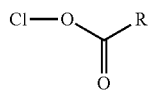

wherein
R is a hydrophobic group and is chosen from:
an alkyl group, linear or branched, containing 1 to 1000 carbon atoms, in particular the groups —(CH$_2$)$_{14}$—CH$_3$ or —(CH$_2$)$_{16}$—CH$_3$,
a linear or branched alkenyl group, containing 2 to 1000 carbon atoms and having at least 1 double bond C═C, in particular the groups —(CH$_2$)$_7$—CH═CH—CH$_2$—(CH$_2$)$_7$—CH$_3$ or —(CH$_2$)$_7$—CH═CH—(CH$_2$)$_7$—CH$_3$.

According to another particular aspect, the invention relates to a preparation process comprising a step of mixing between
a protein, in particular gliadin or gelatin comprising hydrophobic groups covalently bound to said protein, and
an α-cyclodextrin (CD) in the form of a monomer,
and in particular comprising a step of mixing between a gliadin or gelatin involving the amine function and/or the carboxyl function and/or the hydroxyl function and/or the thiol function, of the hydrophobic groups of formula

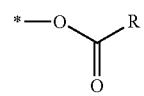

and/or

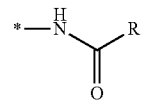

and/or

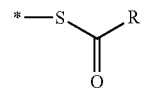

and/or

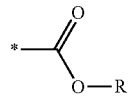

wherein
* represents the protein,
R represents the hydrophobic group and is chosen from:
an alkyl group, linear or branched, containing 1 to 1000 carbon atoms, in particular the groups —(CH$_2$)$_{14}$—CH$_3$ or —(CH$_2$)$_{16}$—CH$_3$,
a linear or branched alkenyl group, containing 2 to 1000 carbon atoms and containing at least one double bond C═C, in particular the groups —(CH$_2$)$_7$—CH═CH═CH$_2$—(CH$_2$)$_7$—CH$_3$ or —(CH$_2$)$_7$—CH═CH—(CH$_2$)$_7$—CH$_3$, and a cyclodextrin of formula

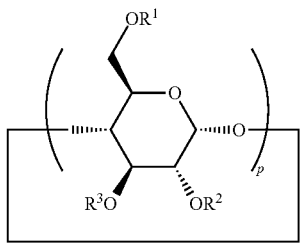

wherein
p is an integer equal to 6,
R1, R2, R3, identical or different, in particular identical, are hydrogen atoms, alkyl groups comprising 1 to 3 carbon atoms, chosen from methyls, ethyls, propyls, isopropyls, amino groups —$NH_2$, ammonium groups —$NH_3^+$, or sulfate groups —$SO_4^{2-}$, and are in particular hydrogen atoms or methyl groups,
with a concentration of between 0.01 and 9000 g/L of aqueous medium, in particular between 1 and 300 g/L, and in particular around 200 g/L of aqueous medium,
said protein, in particular gliadin or gelatin, being
in suspension, at a concentration of between 0.01 and 9000 g/L, in particular between 1 and 300 g/L, and in particular being equal to around 200 g/L, in an aqueous medium, chosen from pure water, an aqueous solution including one or more solutes, in particular one or more salt(s) and/or sugar(s), in particular saccharose or glucose, an injectable solution or suspension or a physiological serum solution, optionally enriched with glucose, an emulsion, a gel, a cream, or any other excipient for pharmaceutical, cosmetic, agrifood or veterinary use,
the percent by weight of said protein, in particular gliadin or gelatin, being between 0.01% and 99.9%, in particular 0.5% to 70%,
the percent by weight of cyclodextrin being between 0.01% and 99.9%, in particular 0.5% and 70%,
the percent by weight of the water or the aqueous medium being between 0.01% and 99.9%, in particular 70% to 99%,
said mixture being produced under agitation, at a temperature of between 0 and 100° C., in particular at a temperature of between 10 and 40° C., and in particular at a temperature equal to around 20° C.

According to yet another aspect, the invention relates to a preparation process, said process not involving the use of solvent and/or surfactant and/or reagent.

According to yet another aspect, the invention relates to a preparation process, said process being capable of containing a purification step.

According to yet another aspect, the invention relates to a preparation process, said process not involving a purification step.

The invention also relates to a gliadin bearing hydrophobic groups having the formula:

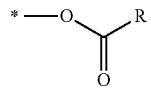

and/or

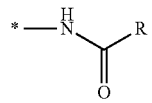

and/or

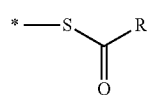

and/or

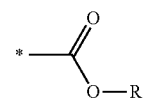

wherein
* represents the protein,
R represents the hydrophobic group and is chosen from:
an alkyl group, linear or branched, containing 1 to 1000 carbon atoms, in particular the groups —$(CH_2)_{14}$—$CH_3$ or —$(CH_2)_{16}$—$CH_3$,
a linear or branched alkenyl group, containing 2 to 1000 carbon atoms and containing at least one double bond C=C, in particular the groups —$(CH_2)_7$—CH=CH=$CH_2$—$(CH_2)_7$—$CH_3$ or —$(CH_2)_7$—CH=CH—$(CH_2)_7$—$CH_3$.

The invention also relates to particles containing an inclusion complex as defined above, for use as drugs, in particular drugs having at least one anti-tumor, anti-pain, anti-inflammatory, antibiotic, antifungal, antiparasitic, enzymatic, hormonal, anxiolytic, antidiabetic, anti-hypertensive, vaccine, antiviral, analgesic, antiepileptic, local and general anesthetic, hypnotic, sedative, antipsychotic, neuroleptic, antidepressant, anticholinergic, cholinomimetic, antimuscarinic, muscarinic, antiadrenergic, antiaryhthmic, antiarthritic, antiasthmatic, anticonvulsant, antihistamine, antiemetic, antineoplastic, antipyretic, antipruritic, antispasmodic, vasodilating, central nervous system-stimulating, decongestant, bone group-stimulating, bone resorption-inhibiting, immunosuppressant, muscle relaxant, psychostimulant, or tranquilizer activity, or in particular drugs containing proteins, peptides or fragments thereof, said proteins, peptides or fragments being natural, recombinant, or chemical products, nucleic acids (ribonucleotides or deoxyribonucleotides), in particular single and double-strand molecules, gene constructs, expression vectors, antisense molecules, and the like.

The invention also relates to particles, comprising an inclusion complex as defined above, for use in the preparation of drugs having at least one anti-tumor, anti-pain, anti-inflammatory, antibiotic, antifungal, antiparasitic, enzymatic, hormonal, anxiolytic, antidiabetic, anti-hypertensive, vaccine, antiviral, analgesic, antiepileptic, local and general anesthetic, hypnotic, sedative, antipsychotic, neuroleptic, antidepressant, anticholinergic, cholinomimetic, antimuscarinic, muscarinic, antiadrenergic, antiarryhthmic, antiarthritic, antiasthmatic, anticonvulsant, antihistamine, antiemetic, antineoplastic, antipyretic, antipruritic, antispasmodic, vasodilating, central nervous system-stimulating, decongestant, bone group-stimulating, bone resorption-inhibiting, immunosuppressant, muscle relaxant, psychostimulant, or tranquilizer activity, or in particular drugs containing proteins, peptides or fragments thereof, said proteins, peptides or fragments being natural, recombinant, or chemical products, nucleic acids (ribonucleotides or deoxyribonucleotides), in particular single and double-strand molecules, gene constructs, expression vectors, anti-sense molecules, and the like.

The invention also relates to particles containing an inclusion complex as defined above, for use as veterinary drugs, in particular anti-tumor, anti-pain, anti-inflammatory, antibiotic, antifungal, antiparasitic, enzymatic, hormonal, anxiolytic, antidiabetic, anti-hypertensive, vaccine, antiviral, analgesic, antiepileptic, local and general anesthetic, hypnotic, sedative, antipsychotic, neuroleptic, antidepressant, anticholinergic, cholinomimetic, antimuscarinic, muscarinic, antiadrenergic, antiarryhthmic, antiarthritic, antiasthmatic, anticonvulsant, antihistamine, anti-emetic, antineoplastic, antipyretic, antipruritic, antispasmodic, vasodilating, central nervous system-stimulating, decongestant, bone group-stimulating, bone resorption-inhibiting, immunosuppressant, muscle relaxant, psychostimulant, or tranquilizer veterinary drugs, or in particular drugs containing proteins, peptides or fragments thereof, said proteins, peptides or fragments being natural, recombinant, or chemical products, nucleic acids (ribonucleotides or deoxyribonucleotides), in particular single and double-strand molecules, gene constructs, expression vectors, anti-sense molecules, and the like.

The invention also relates to the use of particles containing an inclusion complex as defined above as a cosmetic agent, in particular as an anti-aging, depigmenting, bleaching, anti-wrinkle, anti-bag, calming, gumming, exfoliating, nourishing, matting, sebum secretion regulator, astringent, purifying, regenerating, restructuring, retexturizing, skin-protecting, anti-cellulite, firming weight loss, tightening, toning, immediate tightening, immediate toning, anti-dandruff, anti-seborrheic, anti-hair loss, de-tangling, curling, hair strengthening, restructuring, sun protection, self-tanning, tanning accelerator, tanning extender, cicatrization, anti-stretch mark, anti-redness, cell renewal activating, hydrating, fragrance, deodorizing, antitranspirant, cleaning, coloring or preservative agent.

The invention also relates to the use of said particles in makeup.

The invention also relates to the use of particles comprising an inclusion complex as defined above for the implementation of a process for preparing devices, in particular cicatrization dressings, said devices containing said particles, and being capable of releasing said particles or one or more active substance(s) of interest contained in said particles.

The invention also relates to a process for preparing an encapsulation system comprising a step of mixing particles containing inclusion complexes according to the invention, with an active substance of interest used for its properties in the pharmaceutical, medical, paramedical, medical device, cosmetic, veterinary, agrifood, animal feed, agrochemistry, pesticide, cosmetotextile, perfumery or environmental fields or in the paint, construction and/or automobile industry,
said active substance of interest being first dissolved in an aqueous medium such as pure water, an aqueous solution including one or more solutes, in particular one or more salt(s) and/or sugar(s), in particular saccharose or glucose, an injectable solution or suspension or a physiological serum solution enriched with glucose, an emulsion, a gel, a cream, or any other excipient for pharmaceutical, cosmetic, agrifood or veterinary use, said aqueous medium optionally containing a solvent chosen in particular from ethanol or acetone, or a surfactant chosen from the polysorbate derivatives, in particular Tween 80 or Tween 40, in order to obtain particles containing inclusion complexes containing said active substance of interest.

According to a particular embodiment, the process for preparing an encapsulation system according to the invention includes a step of mixing:
    a protein comprising hydrophobic groups covalently bound to the protein by the amine function and/or the carboxyl function and/or the hydroxyl function and/or the thiol function,
    said protein being chosen from elastin, collagen, gliadin, gelatin, keratin, albumin, legumin, vicilin, casein, fibrinogen, insulin, fibrinonectin, a hormone, an enzyme, a coagulation factor, transferrin, fibrillin, an immunoglobulin, a cereal protein (wheat, rice, . . . ), a protein obtained from grains or nuts, a protein obtained from algae, a silk protein, an egg protein, a potato protein, and derivatives of said proteins, and is, in particular, gliadin or gelatin,
    a cyclodextrin designated above,
    an active substance of interest used for its properties in the pharmaceutical, medical, paramedical fields, medical device, cosmetic, veterinary, agrifood, animal feed, agrochemistry, pesticide, cosmetotextile, perfumery or environmental field or in the paint, construction and/or automobile industry,
    the percent by weight of said protein, in particular gliadin or gelatin, being between 0.01% to 99.9%, in particular 0.5% to 70%,
    the percent by weight of cyclodextrin being between 0.01% and 99.9%, in particular 0.5% to 70%,
    the percent by weight of the aqueous medium being between 0.01% and 99.9%, in particular 70% to 99%,
    the percent by weight of the solvent being between 0% and 99.9%, in particular 10% to 80%.

The mixing step of the process for preparing an encapsulation system includes a step of dissolving the active substance of interest in an aqueous medium, followed by the addition to the medium of the protein and the α-cyclodextrin. The mixture is placed under magnetic agitation for 3 days. However, for practically purposes, it is possible to mix all of the components at the same time.

The particles may be isolated:
    by sedimentation, or by centrifugation if they are microparticles (hydrodynamic diameter greater than one micrometer),
    or by ultracentrifugation or by membrane separation methods such as ultrafiltration and microfiltration, if they are nanoparticles (hydrodynamic diameter less than one micrometer).

EXAMPLES

Meaning of the Abbreviations Used
PA: palmitic acid
DS: degree of substitution
IR: Infrared
TEM: transmission electron microscopy
NMR: nuclear magnetic resonance
Characteristics/Types of Analysis Devices Used:
NMR: All of the compounds obtained were analyzed by carbon NMR, $^{13}$C-NMR, of the solid (10 kHz (Bruker-500 MHz spectrometer, Bruker Instrument Inc. Wissembourg, France). The spectra are produced at ambient temperature.
IR spectra (ATR-FTIR, spectrometer FT/IR-4100, JASCO): the principle consists in placing a crystal (diamond) in contact with the sample to be analyzed, before the infrared beam passes through it.
Particle size measurements: The particle sizes were evaluated by the hydrodynamic diameter. The measurements of the mean hydrodynamic diameters of the nanoparticles were performed with a Zetasizer nanoseries Nano-ZS90 of the Malvern Instruments SA company (Orsay, France) by quasi-elastic light scattering. The hydrodynamic diameters of the microparticles were measured by a laser granulometer (MasterSizer 2000) of the Malvern Instruments SA company (Orsay, France).

Transmission electron microscopy (TEM) was used to observe the microparticles and nanoparticles by means of a Philips EM208 microscope and a camera.

Lyophilization of proteins grafted by hydrophobic groups: Certain synthesized protein derivatives were lyophilized using an Alpha 1-2 lyophilizer (Avantec, France) for 24 hours after the solutions were frozen for at least 12 hours.

Details of the Products Used:
All of the solvents: formamide, diethyl ether, ethanol, come from VWR, France.

The wheat gliadin, gelatin, palmitoyl chloride and anhydrous pyridine were provided by Sigma-Aldrich Chemical Co, Saint Quentin Fallavier, France.

The alpha-cyclodextrin comes from Cyclolab (Budapest, Hungary). The hydroxypropyl-β-cyclodextrin (HP-β-CD) was provided by Sigma-Aldrich Chemical Co, Saint Quentin Fallavier, France. The gamma-cyclodextrin (γ-CD) was obtained from Wacker-Chemie (Germany).

Synthesis of Proteins Bearing Hydrophobic Groups

Example 1

Synthesis and Characterization of N-Acylated Gelatin

Gelatin (1 g) was dissolved in 11 mL of formamide. The mixture is heated to 90° C. under continuous magnetic agitation. Then, 3 mL of anhydrous pyridine and 1.2 mL of formamide containing palmitoyl chloride were added to the solution. The quantity of palmitoyl chloride was modified so as to obtain different degrees of substitution (1 g (DS 0.19), 3 g (DS 0.56) and 5 g (DS 1.70)). The gelatins obtained have the following codes, respectively: gelatin-PA1, gelatin-PA2 and gelatin-PA3. After 3 h at 90° C. and 10 minutes at ambient temperature, the mixture is poured into 100 mL of ethanol. The precipitate was collected and washed with 200 mL of ethanol, then with 150 mL of diethylether using a Büchner funnel. The solid is lyophilized for 24 h.

Figure 1:
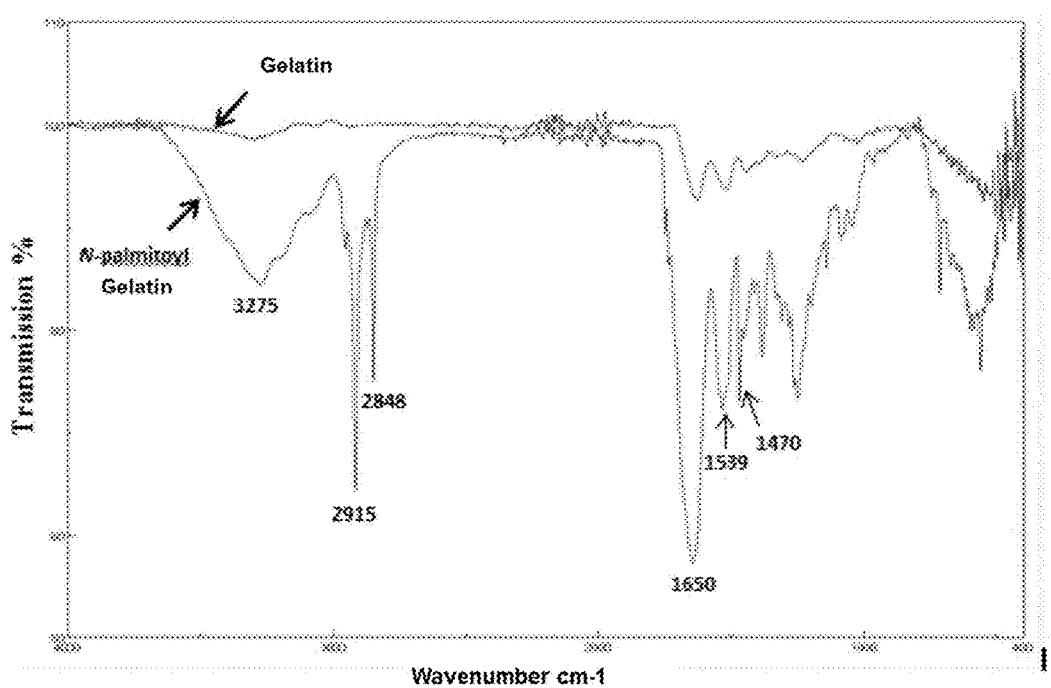
FIG. 1 shows the characteristic IR spectrum of gelatin N-acylated by palmitic acid by comparison with that of native gelatin.

The results are presented in FIG. 1: after acylation, the presence of bands at 1539 and 3275 cm$^{-1}$ corresponding to the NH groups of the amide bond is observed on the IR spectrum. The band observed at 1650 cm$^{-1}$ corresponds to the carbonyl groups of the amide function. The bands at 2915 cm$^{-1}$ and 2848 cm$^{-1}$ and 1470 cm$^{-1}$ correspond to the alkyl chains of the fatty acid.

Example 2

Synthesis and Characterization of N-Acylated Gliadin

Gliadin (1 g) is dissolved in 11 mL of 70% ethanol solution. The mixture is heated to 60° C. under continuous magnetic agitation. Then, 3 mL of pyridine and 1.2 mL of 70% ethanol solution containing palmitoyl chloride are added to the above solution. The quantity of palmitoyl chloride varies from 1 g to 5 g in order to obtain different degrees of substitution. The gliadins obtained have the codes gliadin-PA1 and gliadin-PA2, respectively. After 2 hours at 60° C. and 1 hour at ambient temperature, the mixture is poured into 100 mL of ethanol, previously cooled. The precipitate is collected and washed with 100 mL of ethanol, then 100 mL of diethylether using Büchner funnel. The harvested solid is lyophilized for 24 h.

Figure 2:
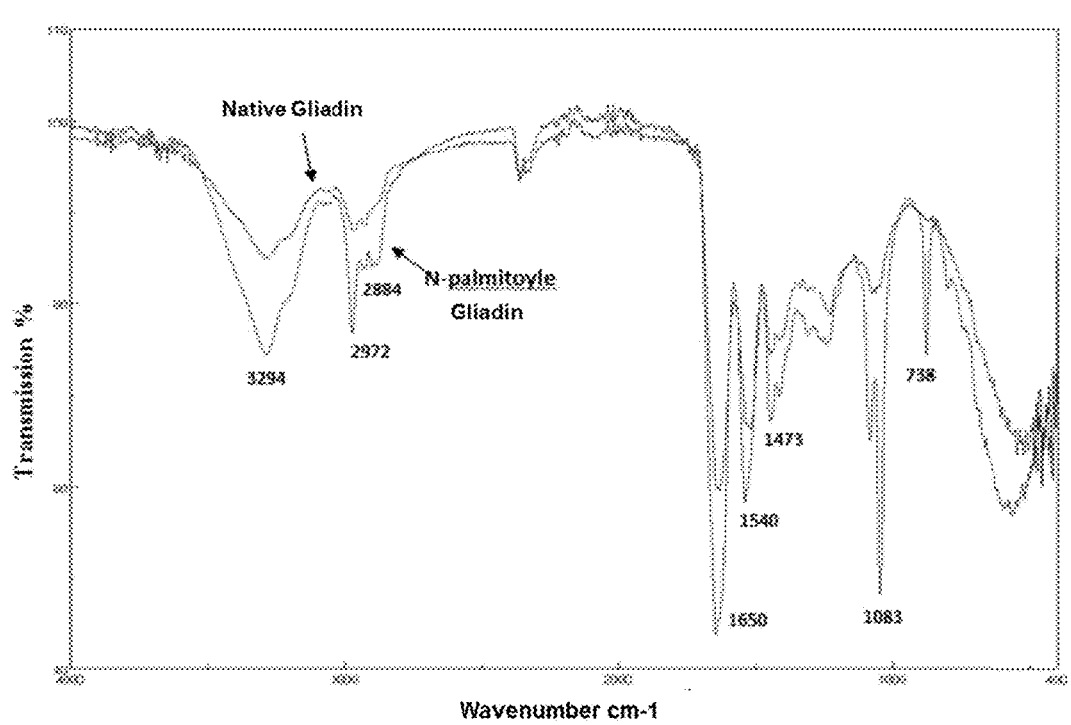
FIG. 2 shows the characteristic IR spectrum of gliadin N-acylated by palmitic acid by comparison with that of native gliadin.

The results are presented in FIG. 2: after acylation, the presence of bands at 1540 and 3294 cm$^{-1}$ are observed on the IR spectrum, corresponding to the —NH groups of the amide function. The band observed at 1650 cm$^{-1}$ corresponds to the carbonyl groups of the amide function. The bands at 2972 cm$^{-1}$ and 2884 cm$^{-1}$ and 1473 cm$^{-1}$ correspond to the alkyl chains of the fatty acid. The band at 1083 cm$^{-1}$ corresponds to the C—C bond of the linear chain of the palmitic acid.

Example 3

Formation of Microparticles and Nanoparticles from a Cyclodextrin and Acylated Gliadins The microparticles and nanoparticles were formed from α-cyclodextrin and protein grafted by palmitic acid. The protocol involves weighting the α-cyclodextrin as well as the acylated protein in a small flask. Then, distilled water is added to the mixture. The same result is obtained regardless of the order in which the ingredients are added. Magnetic or orbital agitation for a maximum of 3 days causes particles to form.

Different gliadins were used:

⇒ Gliadin-PA1 DS 0.22

| Code | Percent by weight (% m/m) gliadin-PA1 DS 0.22% | Percent by weight (% m/m) α-cyclodextrin | $D_h$ (nm) |
|---|---|---|---|
| P01 | 1 | 0 | Cloudy suspension + white aggregates at the bottom |
| P02 | 1 | 10 | 869 ± 183 |
| P03 | 1 | 5 | 1009 ± 244 |
| P04 | 1 | 2.5 | 2004 ± 370 |

Figure 3:
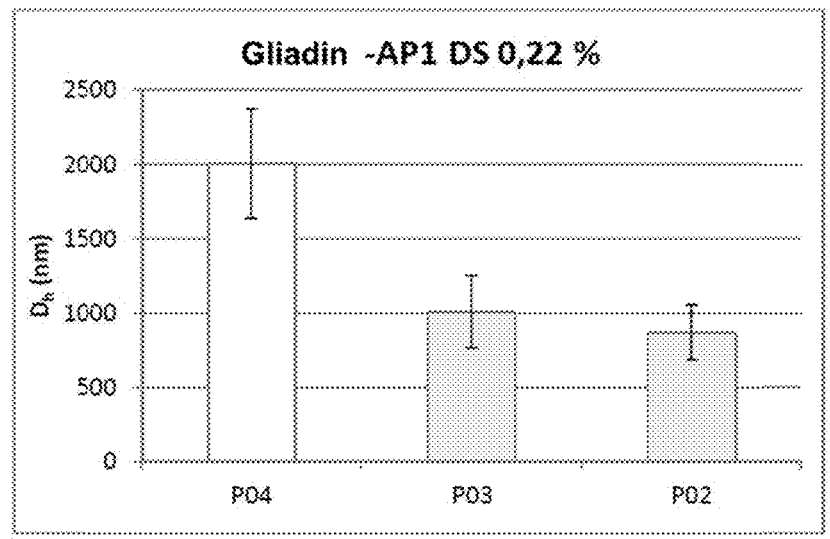
FIG. 3 shows the size of the particles formed from α-cyclodextrin and gliadin grafted by palmitic acid (PA1) with a degree of substitution (DS) of 0.22%.

The results are presented in FIG. 3.

⇒ Gliadin-PA2 DS 0.69

| Code | Percent by weight (% m/m) gliadin-PA2 DS 0.69% | Percent by weight (% m/m) α-cyclodextrin | $D_h$ (nm) |
|---|---|---|---|
| P05 | 1 | 0 | Cloudy suspension + white aggregates at the bottom |
| P06 | 1 | 10 | 705 ± 97 |
| P07 | 1 | 5 | 978 ± 229 |
| P08 | 1 | 2.5 | 1458 ± 370 |

Figure 4:
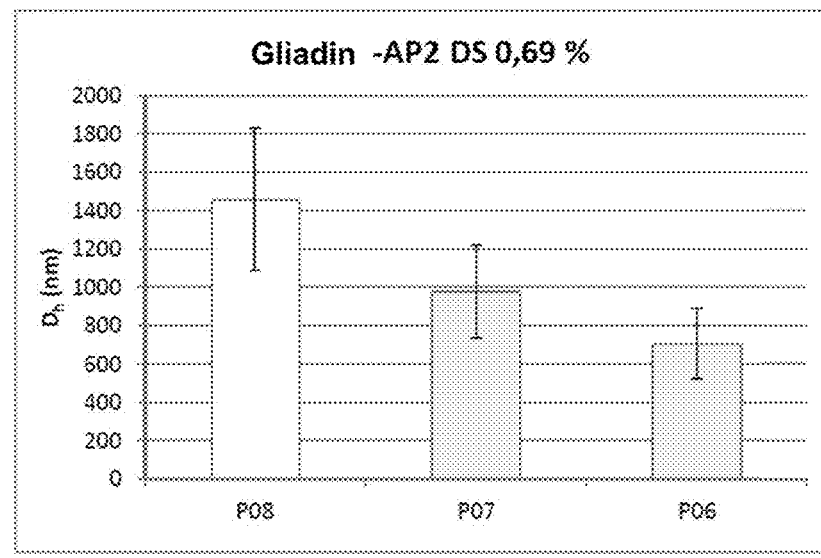
FIG. 4 shows the size of the particles formed from α-cyclodextrin and gliadin grafted by palmitic acid (PA2) with a degree of substitution (DS) of 0.69%.

The results are presented in FIG. 4.

Example 4

Formation of Microparticles and Nanoparticles from α-Cyclodextrin and Acylated Gelatin The microparticles and nanoparticles were formed from α-cyclodextrin and protein grafted by palmitic acid. The protocol involves weighing the α-cyclodextrin as well as the acylated protein in a small flask. Then, distilled water is added to the mixture. The same result is obtained regardless of the order of addition of the ingredients. Magnetic or orbital agitation for a maximum of 3 days causes particles to form.

Different gelatins were used:

⇒ Gelatin-PA1DS 0.19

| Code | Percent by weight (% wt./wt.) gelatin-PA1 DS 0.19% | Percent by weight (% wt./wt.)) α-cyclodextrin | $D_h$ (nm) |
|---|---|---|---|
| P09 | 1 | 0 | Cloudy suspension + white aggregates at the bottom |
| P10 | 1 | 10 | 1432 ± 399 |
| P11 | 1 | 5 | 1808 ± 248 |
| P12 | 1 | 2.5 | 1100 ± 10 |

Figure 5:
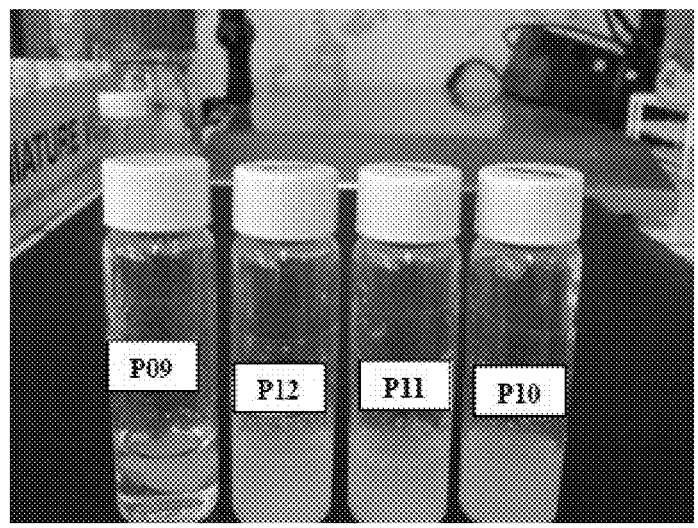
FIG. 5 shows the particles obtained in solution with gelatin grafted by palmitic acid (PA1) with a degree of substitution (DS) of 0.19%.
Figure 6:
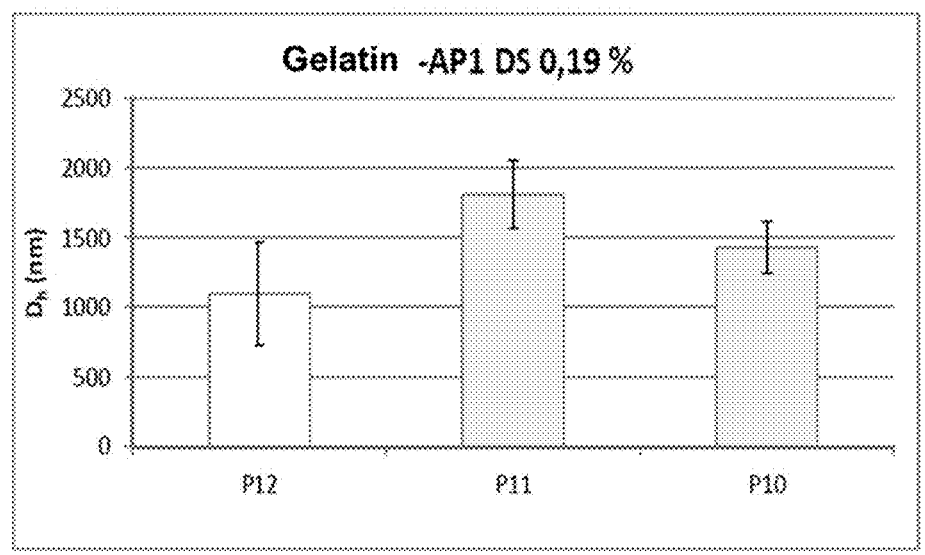
FIG. 6 shows the size of the particles formed from α-cyclodextrin and gelatin grafted by palmitic acid (PA1) with a degree of substitution (DS) of 0.19%.

The results are presented in FIG. 5 and in FIG. 6.

⇒ Gelatin-PA2 DS 0.59%

| Code | Percent by weight (% wt./wt.)) gelatin-PA2DS 0.59% | Percent by weight (% wt./wt.)) α-cyclodextrin | $D_h$ (nm) |
|---|---|---|---|
| P13 | 1 | 0 | A large aggregate |
| P14 | 1 | 10 | 1155 ± 48 |
| P15 | 1 | 5 | 1802 ± 219 |
| P16 | 1 | 2.5 | 1155 ± 48 |

Figure 7:
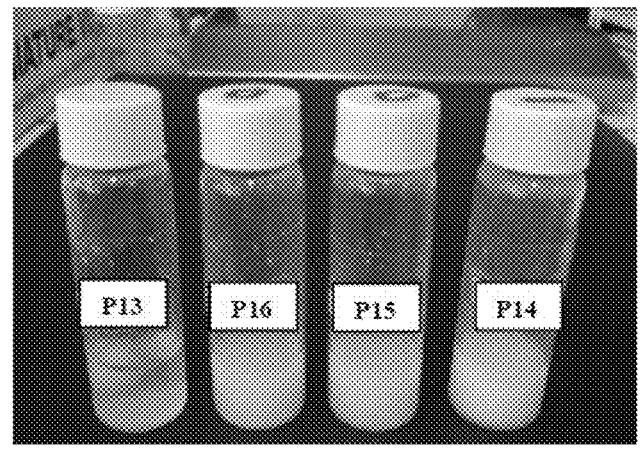
FIG. 7 shows the size of the particles formed from α-cyclodextrin and gelatin grafted by palmitic acid (PA2) with a degree of substitution (DS) of 0.59%.
Figure 8:
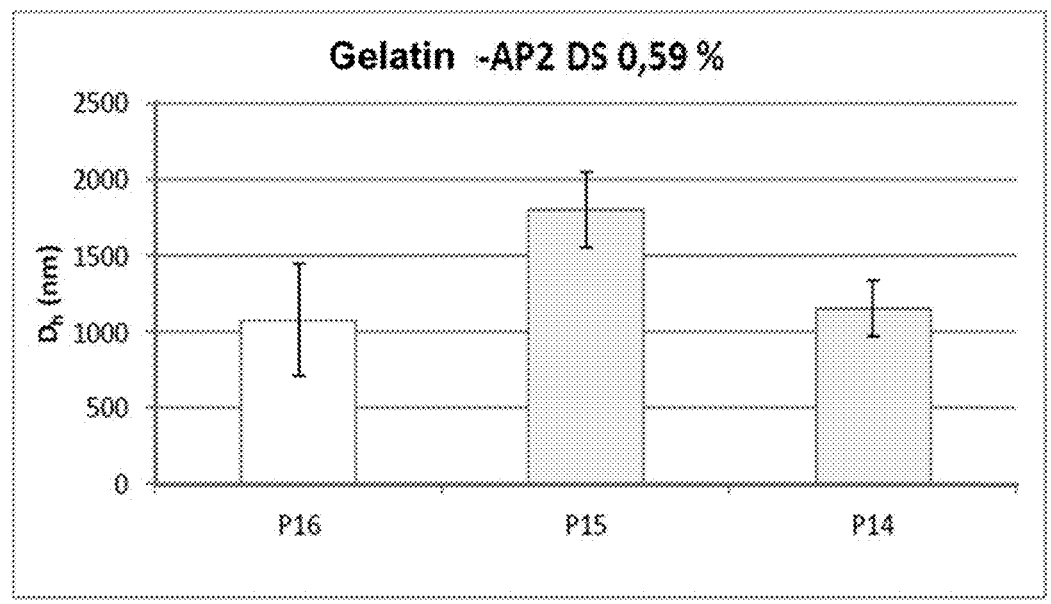
FIG. 8 shows the size of the particles formed from α-cyclodextrin and gelatin grafted by palmitic acid (PA2) a degree of substitution (DS) of 0.59%.
Figure 9:
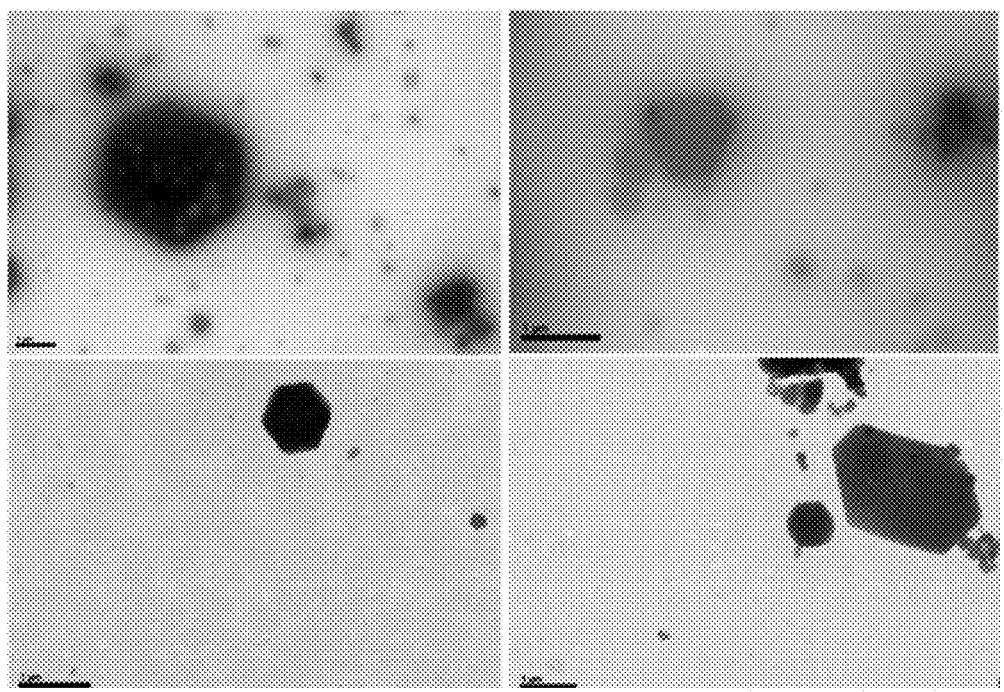
FIG. 9 shows images of gelatin particles observed by transmission electron microscopy (Gelatin PA2DS 0.59 ¹/₁₀% m/m).
Figure 10:
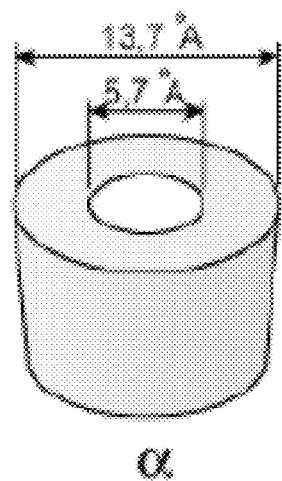
FIG. 10 shows α-cyclodextrin. In the figure, the dimensions are indicated in Angstroms.

The results are presented in FIG. 7, FIG. 8 and FIG. 9.

Comparative Example 5

Experiments Performed by Interacting the Amphiphilic Proteins with the Beta-Cyclodextrin Derivatives (β-CD)

| | Code | Percent by weight acylated protein (% wt./wt.)) | Percent by weight HP-β-CD (% wt./wt.)) | Observations |
|---|---|---|---|---|
| gliadin-PA2 DS 0.69% | P21 | 1 | 10 | No formation of particles. Large aggregates |
| gelatin-PA3 DS 1.70% | P22 | 1 | 10 | |

In the presence of β-cyclodextrin, no particle is formed.

| | Code | Percent by weight acylated protein (% wt./wt.)) | Percent by weight Me-β-CD (% wt./wt.)) | Observations |
|---|---|---|---|---|
| gliadin-PA2 DS 0.69% | P23 | 1 | 10 | No formation of particles. Large aggregates |
| gelatin-PA3 DS 1.70% | P24 | 1 | 10 | |

In the presence of β-cyclodextrin, no particle is formed.

Comparative Example 6

Experiments Performed by Interacting the Amphiphilic Proteins with the Gamma-Cyclodextrin Derivatives (γ-CD)

| | Code | Percent by weight acylated protein (% wt./wt.)) | Percent by weight γ-CD (% wt./wt.)) | Observations |
|---|---|---|---|---|
| gliadin-PA2 DS 0.69% | P25 | 1 | 10 | No formation of particles. Large |

-continued

| | Code | Percent by weight acylated protein (% wt./wt.)) | Percent by weight γ-CD (% wt./wt.)) | Observations |
|---|---|---|---|---|
| gelatin-PA3 DS 1.70% | P26 | 1 | 10 | aggregates |

In the presence of γ-cyclodextrin, no particle is formed.

The invention claimed is:

1. An inclusion complex formed by the interaction between
    at least one protein selected from the group consisting of elastin, collagen, gliadin, gelatin, keratin, legumin, vicilin, casein, fibrinonectin and fibrillin, said protein substituted by hydrophobic groups covalently bound to said protein, and
    at least one α-cyclodextrin (CD) in the form of a monomer,
the protein and the cyclodextrin being non-covalently bound, wherein the hydrophobic groups by which said protein is substituted are alkyl groups, linear or branched.

2. The inclusion complex according to claim 1, wherein the protein has a molar mass of between 100 Da and 1,000,000 kDa, and wherein the degree of substitution of the protein by the hydrophobic groups is between 0.001 and 100%.

3. The inclusion complex according to claim 1, wherein the ratio between the cyclodextrin concentration in g/L and that of the protein is between $10^{-6}$ and 900,000.

4. The inclusion complex according to claim 1, wherein the hydrophobic groups are covalently fixed to the protein by an amine function and/or a carboxyl function and/or a hydroxyl function and/or a thiol function.

5. The inclusion complex according to claim 1, wherein the cyclodextrin (CD) has the formula

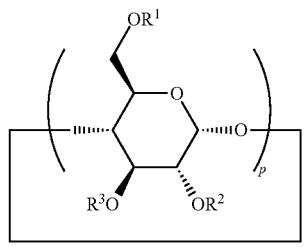

wherein
    p is an integer equal to 6,
    R1, R2, R3, identical or different, are hydrogen atoms, alkyl groups comprising 1 to 3 carbon atoms, chosen from methyls, ethyls, propyls, isopropyls, amino groups —NH$_2$, ammonium groups —NH$_3^+$, or sulfate groups —SO$_4^{2-}$,
said CD being in the form of a monomer.

6. The inclusion complex according to claim 1, wherein the protein is gliadin or gelatin, bearing hydrophobic groups fixed by an amine function and/or a carboxyl function and/or a hydroxyl function and/or a thiol function, and representing groups of formula:

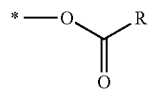

and/or

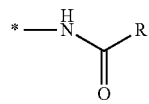

and/or

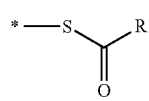

and/or

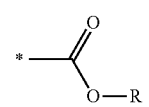

wherein
    * represents the protein,
    R represents the hydrophobic group and is selected from the group consisting of:
        an alkyl group, linear or branched, containing 1 to 1000 carbon atoms, and an alkenyl group, linear or branched, containing 2 to 1000 carbon atoms and containing at least one double bond C=C.

7. A process for preparing an inclusion complex according to claim 1, comprising a step of mixing at least
    a protein selected from the group consisting of elastin, collagen, gliadin, gelatin, keratin, legumin, vicilin, casein, fibrinonectin and fibrillin, said protein substituted by hydrophobic groups covalently bound to said protein, and
    a α-cyclodextrin (CD) in the form of a monomer, said protein substituted by hydrophobic groups of formula

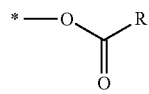

and/or

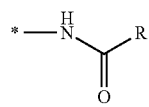

and/or

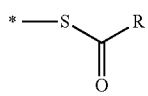

and/or

wherein
* represents the protein,
R represents the hydrophobic group and is selected from the group consisting of:
an alkyl group, linear or branched, containing 1 to 1000 carbon atoms,
an alkenyl group, linear or branched, containing 2 to 1000 carbon atoms and containing at least one double bond C=C, in order to obtain an inclusion complex wherein said protein and said cyclodextrin are non-covalently bound.

* * * * *